US00PP36218P2

(12) United States Plant Patent
van 't Hul

(10) Patent No.: US PP36,218 P2
(45) Date of Patent: Oct. 22, 2024

(54) ***HEMEROCALLIS* PLANT NAMED 'Huhe01'**

(50) Latin Name: ***Hemerocallis* hybrid**
Varietal Denomination: Huhe01

(71) Applicant: Michel van 't Hul, Heteren (NL)

(72) Inventor: Michel van 't Hul, Heteren (NL)

( * ) Notice: Subject to any disclaimer, the term of this patent is extended or adjusted under 35 U.S.C. 154(b) by 0 days.

(21) Appl. No.: 18/438,423

(22) Filed: Feb. 10, 2024

(30) Foreign Application Priority Data

Mar. 27, 2023 (QZ) ..... PBR 2023/0736

(51) Int. Cl.
*A01H 6/00* (2018.01)
*A01H 5/02* (2018.01)

(52) U.S. Cl.
USPC ..... Plt./312

(58) Field of Classification Search
USPC ..... Plt./312
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hemerocallis* plant named 'Huhe01' that is characterized by its lowers that last over 7 days, its unique flower coloration; opening lime-green-yellow, changing to yellow and then changing to orange as the flowers mature, and its healthy, blue-green foliage.

3 Drawing Sheets

Botanical classification: *Hemerocallis* hybrid
Cultivar designation: 'Huhe01'

CROSS REFERENCE TO A RELATED APPLICATION

This application claims priority to European Community Plant Variety Office (CPVO) filed on Mar. 27, 2023, application No. 2023/0736. The Applicant received the information for the Plant breeders' rights application directly from the Inventor.

BACKGROUND OF THE INVENTION

The present invention relates to a new and distinct cultivar of *Hemerocallis* plant of hybrid origin, botanically known as *Hemerocallis* 'Huhe01' and will be referred to hereafter by its cultivar name, 'Huhe01'. 'Huhe01' is a new cultivar of herbaceous daylily grown for use in the landscape and as a container plant.

The new cultivar arose from a breeding program by the inventor at his nursery in Arnhem, The Netherlands. The new cultivar arose from pollination of *Hemerocallis* 'Summer Dragon' (not patented) as the female parent with pooled pollen from propriety plants from the Inventor's breeding program in 2005. The male parent is unknown. 'Huhe01' was selected as a single unique plant from the resulting seedlings in 2008.

Asexual propagation of the new cultivar was first accomplished by division in Elst, The Netherlands in 2008 by the Inventor. Asexual propagation by division and tissue culture using meristematic tissue has determined that the characteristics of this cultivar are stable and are reproduced true to type in successive generations.

SUMMARY OF THE INVENTION

The following traits have been repeatedly observed and represent the characteristics of 'Huhe01'. These attributes in combination distinguish 'Huhe01' as a new and distinct cultivar of *Hemerocallis*.

1. 'Huhe01' exhibits flowers that last over 7 days.
2. 'Huhe01' exhibits unique flower coloration; opening lime-green-yellow, changing to yellow and then changing to orange as the flowers mature.
3. 'Huhe01' exhibits healthy, blue-green foliage.

The female parent of 'Huhe01' is similar to 'Huhe01' in flower size and in having evergreen foliage. The female parent of 'Huhe01' differs from 'Huhe01' in having flowers that are yellow in color with a red center and last for 1 day. 'Huhe01' can be most closely compared to *Hemerocallis* cultivars 'Green Flutter' (not patented) and 'Condilla' (not patented). 'Green Flutter' differs from 'Huhe01' in having yellow-green flowers with a green throat that last 1 day. 'Condilla' differs from 'Huhe01' in having double flowers that are orange in color and last up to 30 hours.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Monrovia, Visions Pictures, The National Gardening Association, Plantipp, issuu, and American Horticulture Society.

BRIEF DESCRIPTION OF THE DRAWINGS

The accompanying color photographs illustrate the overall appearance and distinct characteristics of the new *Hemerocallis*. The photographs were taken of a 3-year-old plant as grown outdoors in a 28-cm container in Den Burg, The Netherlands.

The photograph in FIG. 1 provides a side view of 'Huhe01' in bloom.

Figure 1:
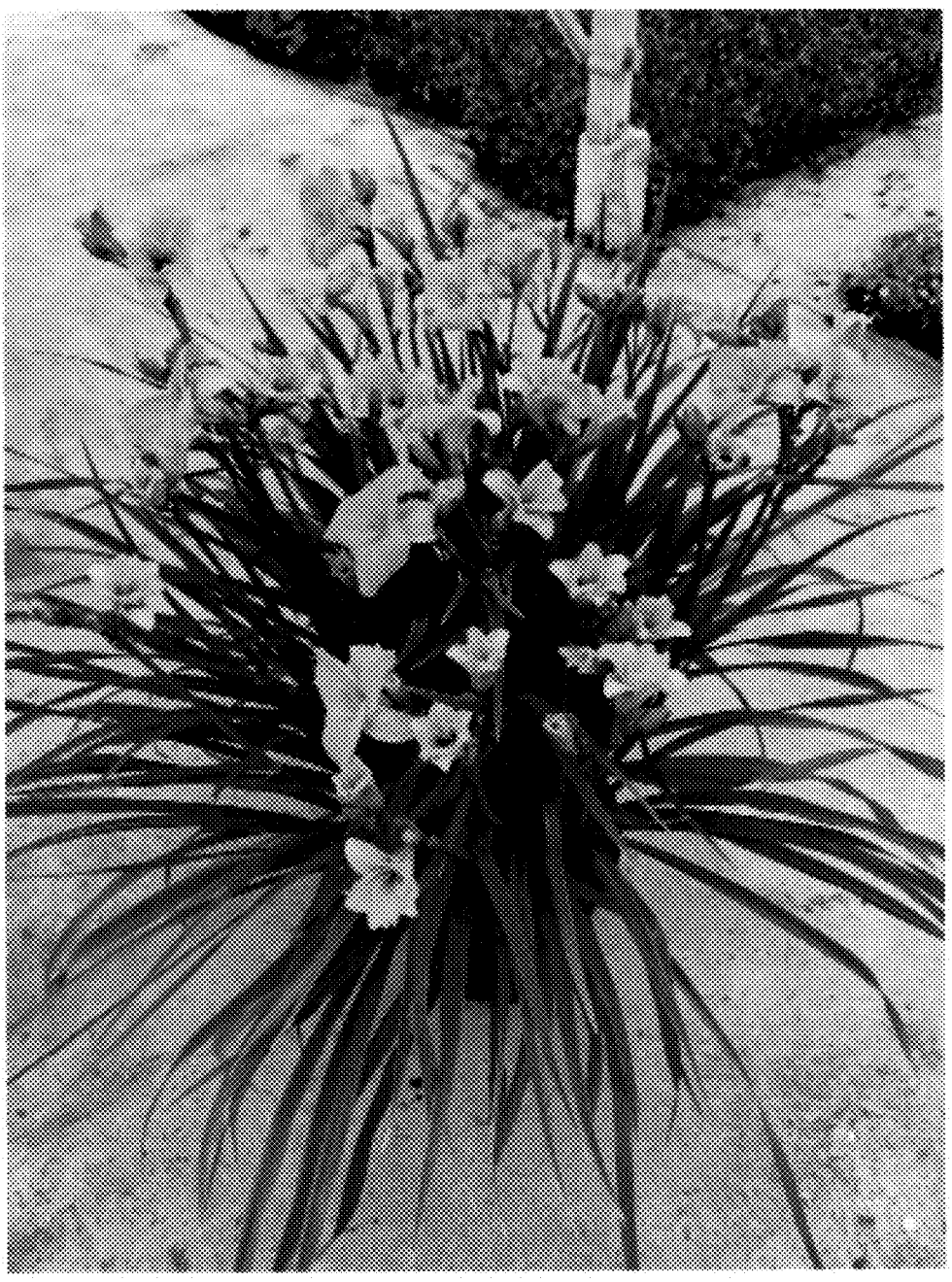
Figure 2:
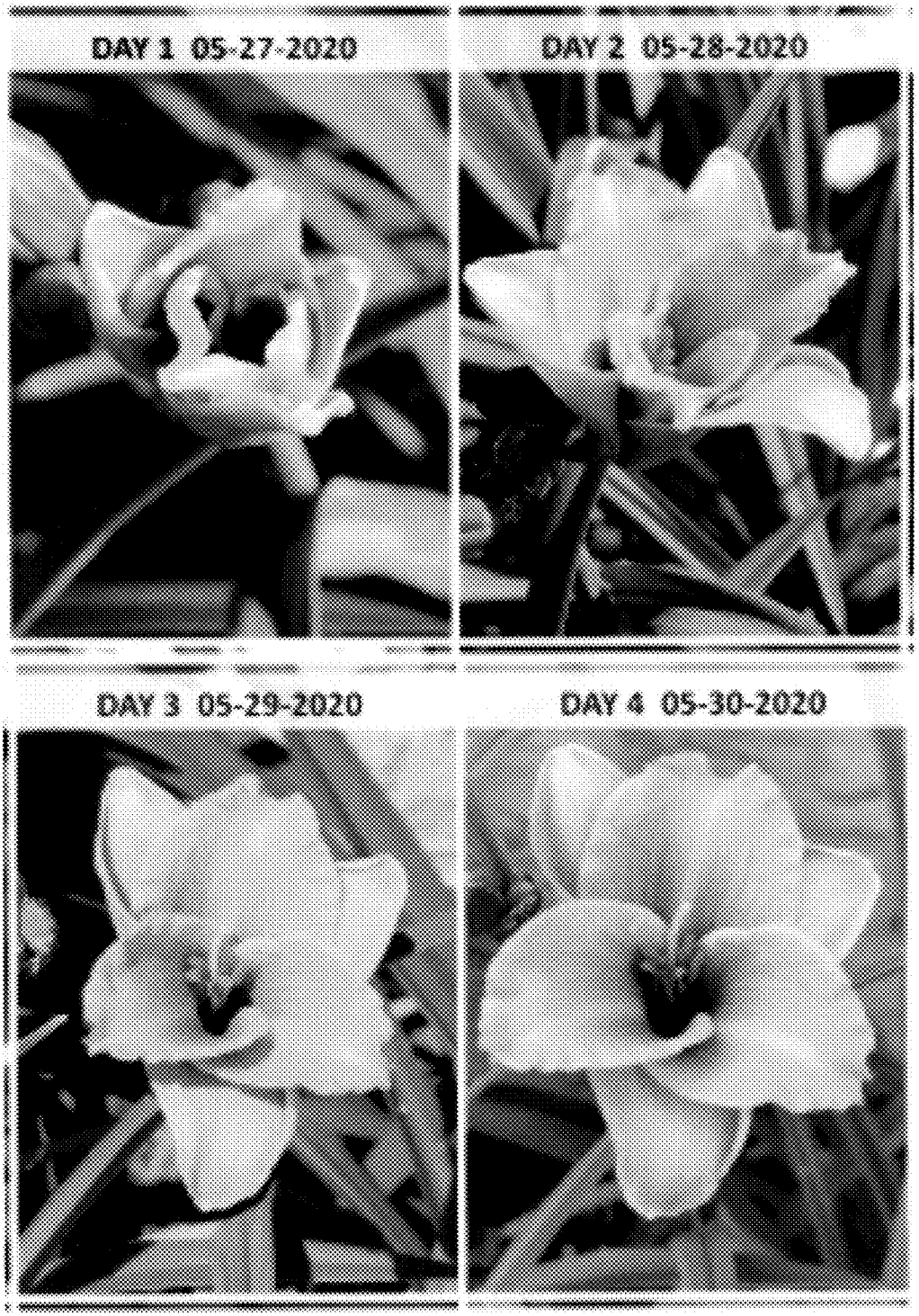

The photograph in FIG. 2 provides a close-up view of a flower of 'Huhe01' 1 day, 2 days, 3 days and 4 days after opening.

Figure 3:
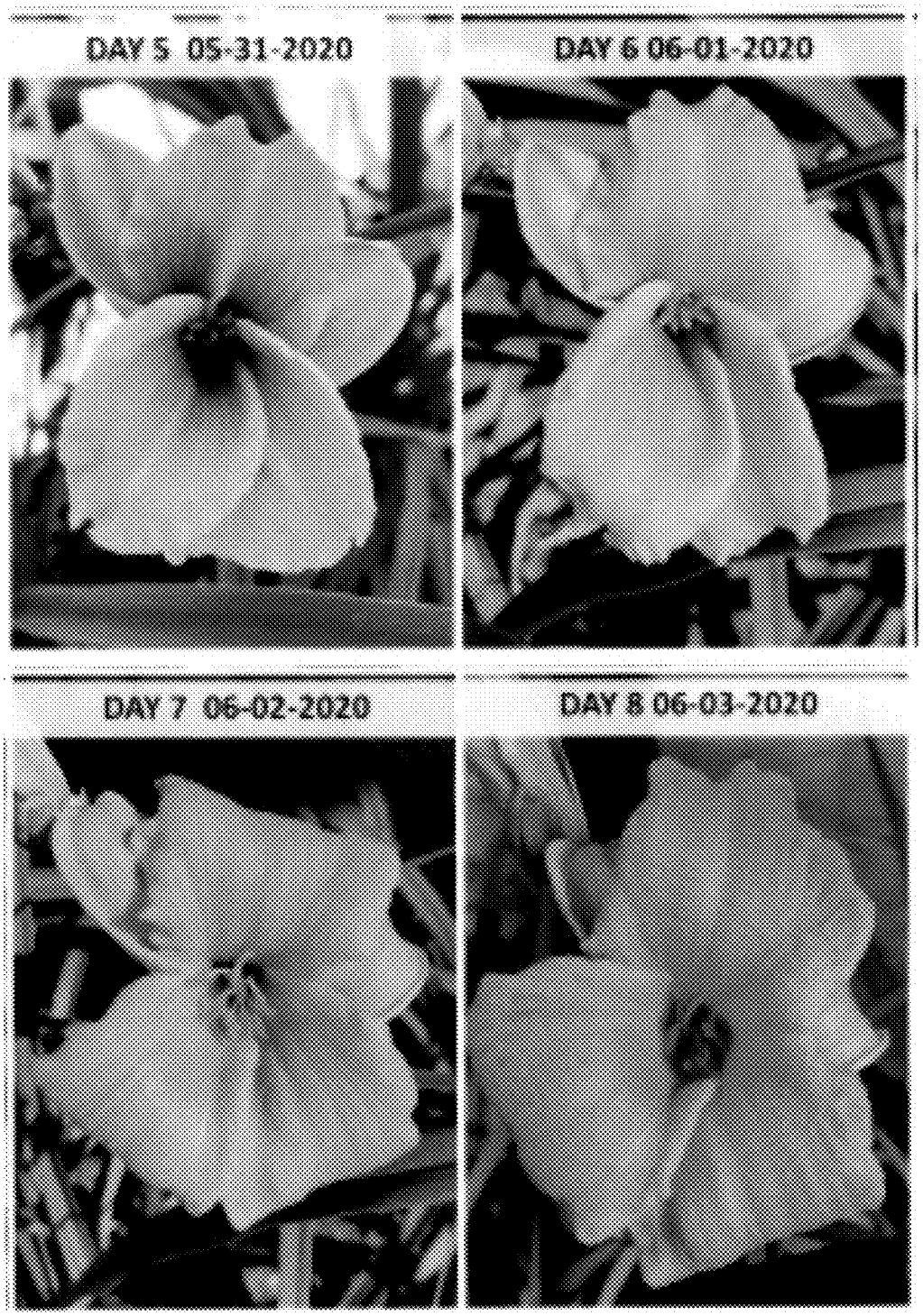

The photograph in FIG. 3 provides a close-up view of a flower of 'Huhe01' 5 days, 6 days, 7 days and 8 days after opening. The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of 3-year-old plants of the new cultivar as grown outdoors in 28-cm containers in Den Burg, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period*.—May through August in Belgium.
*Plant type*.—Evergreen perennial.
*Plant habit*.—Upright with arching leaves.
*Height and spread*.—Average of 76 cm in height, 1.1 m in width as a 3-year-old plant grown in a container.
*Cold hardiness*.—At least in U.S.D.A. Zone 6.
*Diseases and pests*.—No susceptibility or resistance to diseases or pests has been observed.
*Root description*.—Fleshy.
*Propagation type*.—Division and tissue culture.
*Root development*.—Average of 4 to 6 weeks to initiate roots in spring on a division and 4 to 6 weeks to fully root a rooted division in a 12-cm container.
*Growth rate*.—Vigorous.
*Branching*.—Basal.

Foliage description:

*Leaf shape*.—Linear.
*Leaf division*.—Simple.
*Leaf base*.—Sheathing.
*Leaf apex*.—Acute.
*Leaf venation*.—Parallel, 137B in color on both surfaces.
*Leaf margins*.—Entire.
*Leaf attachment*.—Sessile, decurrent, no petioles.
*Leaf arrangement*.—Basal rosette.
*Leaf orientation*.—Held upright to pendulant.
*Leaf surface*.—Both surfaces glabrous.
*Leaf color*.—Upper surface; 137A to 137B, lower surface; 144B.
*Leaf size*.—Average of 64 cm in length, an average of 2 cm in width.
*Leaf quantity*.—Average of 10 leaves per shoot.

Flower description:

*Inflorescence type*.—Scape bearing a panicle of single flowers opening in succession.
*Lastingness of flowers*.—Average of 7 days, self-cleaning.
*Flower size*.—10 cm in diameter, 5.5 cm in depth.
*Flower fragrance*.—None.
*Flower number*.—An average of 22 flowering stems per plant, 4 to 6 buds per flowering stem, an average of 48 flowers and 40 buds per plant.
*Flower aspect*.—Upright to outward.
*Flower type*.—Campanulate, freely flowering.
*Flower bud*.—Oblanceolate in shape, young bud 6 mm in length, 5 mm in diameter, before burst 2.5 cm in length, 1 cm in diameter, surface is glabrous, color; 144B to 144C, veins 154B.
*Petals* (*inner tepals*).—3, oblanceolate in shape, reflexed, average of 5.3 cm in length and 3.6 cm in width, margins entire and undulate, both surfaces glabrous and velvety, apex obtuse, base fused, color: young upper and lower surface; a blend of 154A to 154B and 144B, mature and aging upper and lower surface; a blend of 5A, 144B, 21B, and N25C to N25D.
*Sepals* (*outer tepals*).—3, rotate in arrangement, average of 5.2 cm in length, 3.4 cm in width, oblanceolate in shape, margins are entire and undulate, obtuse apex, base fused, both surfaces glabrous and velvety, color: young upper and lower surface; a blend of 154A to 154B and 144B, mature and aging upper and lower surface; a blend of 5A, 144B, and 21B.
*Peduncles*.—Round in shape, 62 cm in length, 7 mm in diameter, strong, 137B in color, glabrous surface.
*Pedicels*.—Round in shape, strong, 3 cm in length, 5 mm in diameter, strong, 137B in color, glabrous surface.

Reproductive Organs:

*Gynoecium*.—Pistil; 1, average of 3.7 cm in length, 1.5 mm in width, style; 3.7 cm in length, 144D in color, stigma; not distinguishable, ovary; 6 mm in length, 4 mm in width, 143C in color.
*Androecium*.—Stamens; 6, anthers; dorsifixed in shape, 6 mm in length, 2 mm in width, 200A in color, filament; 3 cm in length, 1 mm in width, color; 13A, proximal end 1B, pollen; abundant in quantity and 21A in color.
*Fruit/Seeds*.—None observed to date.

It is claimed:

1. A new and distinct cultivar of *Hemerocallis* plant named 'Huhe01' as herein illustrated and described.

* * * * *